United States Patent [19]

Charonis

[11] Patent Number: 5,120,828
[45] Date of Patent: Jun. 9, 1992

[54] SYNTHETIC POLYPEPTIDE WITH LAMININ ACTIVITY

[75] Inventor: Aristidis S. Charonis, Minneapolis, Minn.

[73] Assignee: Regents of the University of Minnesota, Minneapolis, Minn.

[21] Appl. No.: 348,407

[22] Filed: May 8, 1989

[51] Int. Cl.⁵ .................. A61K 37/02; C07K 7/08
[52] U.S. Cl. .................................. 530/326; 514/13
[58] Field of Search ............ 530/324, 326; 514/12, 514/13

[56] References Cited

U.S. PATENT DOCUMENTS 4,565,789  1/1986  Liotta et al. ............... 436/504
4,578,079  3/1986  Ruoslahti et al. ............ 623/11

OTHER PUBLICATIONS

Sasaki et al., Proc. Natl. Acad. Sci., vol. 84, pp. 935-939, 1987.
Charonis et al., J. Cell Biology, vol. 107, pp. 1253-1260, 1988.
Sasaki et al., J. Biol. Chem., vol. 262, pp. 17111-17117, 1987.
Charonis et al., J. Cell Biol., vol. 103, pp. 1689-1697, 1986.
R. Timpl and H. Rhode, J. Biol. Chem., 254, 9933-9937 (1979).
R. Timpl and M. Dziadek, Intern. Rev. Exp. Path., 29, 1-112 (1986).
J. Engel et al., J. Mol. Biol., 150, 97-120 (1981).
A. S. Charonis et al., J. Cell Biol., 100, 1848-1853 (1985).
G. W. Laurie et al., J. Mol. Biol., 189, 205-216 (1986).
V. P. Terranova et al., Proc. Natl. Acad. Sci. USA, 80, 444-448 (1983).
P. D. Yurchenco et al., J. Biol. Chem., 260, 7636-7644 (1985).
H. Lesot et al., EMBO J., 2, 861-865 (1983).
H. L. Malinoff and M. S. Wicha, J. Cell Biol., 96, 1475-1479 (1983).
A. Horwitz et al., J. Cell Biol., 101, 2134-2144 (1985).
D. D. Roberts et al., Proc. Natl. Acad. Sci. USA, 82, 1306-1310 (1985).
U. Ott et al., Eur. J. Biochem., 123, 63-72 (1982).
D. Edgar et al., EMBO J., 3, 1463-1468 (1986).
L. A. Liotta, Am. J. Path., 117, 339-348 (1984).
J. B. McCarthy et al., Cancer Met. Rev., 4, 125-152 (1985).
M. Sasaki et al., J. Biol. Chem., 263, 16536-16544 (1988).
D. M. Shotton et al., J. Mol. Biol., 131, 303-329 (1979).
R. M. Hewick et al., J. Biol. Chem., 256, 7990-7997 (1981).
J. Furcht et al., Bio. Mol. Gen. Cancer Met.; K. Lapis et al., eds. (1985) at 43-53.
D. W. Kennedy et al., J. Cell. Phys., 114, 257-262 (1983).
J. Kyte and R. F. Doolittle, J. Mol. Biol., 157, 105-132 (1982).
E. C. Tsilibary and A. S. Charonis, J. Cell Biol., 103, 388(a) (1986).

Primary Examiner—Lester L. Lee
Assistant Examiner—Avis M. Davenport

[57] ABSTRACT

A polypeptide having the following formula is provided: arg-ile-gln-asn-leu-leu-lys-ile-thr-asn-leu-arg-ile-lys-phe-val-lys; which can bind heparin and promote cellular adhesion.

Medical devices such as prosthetic implants, percutaneous devices and cell culture substrates coated with a composition including the polypeptide are also provided.

1 Claim, 9 Drawing Sheets

```
         10         20         30         40         50         60         70
QEPEFSYGCA EGSCYPATGD LLIGRAQKLS VTSTCGLHKP EPYCIVSHLQ EDKKCFICDS RDPYHETLNP
         80         90        100        110        120        130        140
DSHLIENWT  TFAPNRLKIW WQSENGVENV TIQLALEAEF HFTHLIMTFK TFRPAAMLIE RSSDFGKTWG
        150        160        170        180        190        200        210
VYRYFAYDCE SSFPGISTGP MKKVDDIICD SRYSDIEPST EGEVIFRALD PAFKIEDPYS PRIQNLLKIT
        220        230        240        250        260        270        280
NLRIKFVKLH TLGDNLLDSR MEIREKYYYA VYDMVVRGNC FCYGHASECA PVDGVNEEVE GMVHGHCMCR
        290        300        310        320        330        340        350
HNTKGLNCEL CMDFYHDLPW RPAEGRNSNA CKKCNCNEHS SSCHFDMAVF LATGNVSGGV CDNCQHNTMG
        360        370        380        390        400        410        420
RNCEQCKPFY FQHPERDIRD PNLCEPCTCD PAGSENGGIC DGYTDFSVGL IAGQCRCKLH VEGERCDVCK
        430        440        450        460        470        480        490
EGFYDLSAED PYGCKSCACN PLGTTPGGNP CDSETGYCYC KRLVTGQRCD QCLPQHWGLS NDLDGCRPCD
        500        510        520        530        540        550        560
CDLGGALNNS CSEDSGQCSC LPHMIGRQCN EVESGYYFTT LDHYIYEAEE ANLGPGVVV  ERQYIQDRIP
        570        580        590        600        610        620        630
SWTGPGFVRV PEGAYLEFFI DNIPYSMEYE ILIRYPQLP  DHWEKAVITV QRPGKIPASS RCGNTVPDDD
        640        650        660        670        680        690        700
NQWSLSPGS  RYWLPRPVC  FEKGMNYTVR LELPQYTASG SDVESPYTFI DSLVLMPYCK SLDIFTVGGS
        710        720        730        740        750        760        770
GDGEVTNSAW ETFQRYRCLE NSRSWKTPM  TDVCRNIIFS ISALIHQTGL ACECDPQGSL SSVCDPNGGQ
        780        790        800        810        820        830        840
CQCRPNVVGR TCNRCAPGTF GFGPNGCKPC DCHLQGSASA FCDAITGQCH CFQGIYARQC DRCLPGYWGF
        850        860        870        880        890        900        910
PSCQPCQNG  HALDCDTVTG ECLSCQDYTT GHNCERCLAG YYGDPIIGSG DHCRPCPCPD GPDSGRQFAR
        920        930        940        950        960        970        980
SCYQDPVTLQ LACVCDPGYI GSRCDDCASG FFGNPSQFGG SCQPCQCHHN IDTTDPEACD KDTGRCLKCL
        990       1000       1010       1020       1030       1040       1050
YHTEGDHCQL CQYGYYGDAL RQDCRKCVCN YLGTVKEHCN GSDCHCDKAT GQCSCLPNVI GQNCDRCAPN
       1060       1070       1080       1090       1100       1110       1120
TWQLASGTGC GPCNCNAAHS FGPSCNEFTG QCQCMPGFGG RTCSECQELF WGDPDVECRA CDCDPRGIET
       1130       1140       1150       1160       1170       1180       1190
PQCDQSTGQC VCVEGVEGPR CDKCTRGYSG VFPDCTPCHQ CFALWDAIIG ELTNRTHKFL EKAKALKISG
       1200       1210       1220       1230       1240       1250       1260
VIGPYRETVD SVEKKVNEIK DILAQSPAAE PLKNIGILFE EAEKLTKDVT EKMAQVEKL  TDTASQSNST
```

FIG. 2A

```
         1270       1280       1290       1300       1310       1320       1330
   AGELGALQAG AESLDKTVKE LAEQLEFIKN SDIQGALDSI TKYFQMSLEA EKRVNASTTD PNSTVEQSAL 1340       1350       1360       1370       1380       1390       1400
   TRDRVEDLML ERESPFKEQQ EEQARLLDEL AGKLQSLDLS AAAQMTCGTP PGADCSESEC GGPNCRTDEG 1410       1420       1430       1440       1450       1460       1470
   EKKCGGPGCG GLVTVAHSAW QKAMDFDRDV LSALAEVEQL SKMVSEAKVR ADEAKQNAQD VLLKTNATKE 1480       1490       1500       1510       1520       1530       1540
   KVDKSNEDLR NLIKQIRNFL TEDSADLDSI EAVANEVLKS GNASTPQQLQ NLTEDIRERV ETLSQVEVIL 1550       1560       1570       1580       1590       1600       1610
   QQSAADIARA ELLLEEAKRA SKSATDVKVT ADMVKEALEE AEKAQVAAEK AIKQADEDIQ GTQNLLTSIE 1620       1630       1640       1650       1660       1670       1680
   SETAASEETL TNASQRISKL ERNVEELKRK AAQNSGEAEY IEKVVYSVKQ NADDVKKTLD GELDEKYKKV 1690       1700       1710       1720       1730       1740       1750
   ESLIAQKTEE SADARRKAEL LQNEAKTLLA QANSKLQLLE DLERKYEDNQ KYLEDKAQEL VRLEGEVRSL

1760
   LKDISEKVAV YSTCL
```

FIG. 2B

DOMAIN I : 1410-1765
DOMAIN A : 1377-1409
DOMAIN II : 1158-1376
DOMAIN III : 751-1157
DOMAIN IV : 520-750
DOMAIN V : 249-519
DOMAIN VI : 1-248

SYNTHETIC POLYPEPTIDE WITH LAMININ ACTIVITY

CROSS-REFERENCE TO RELATED APPLICATION

This invention was made with Government support under contract number DK 39868-02 by the U.S. National Institutes of Health. The Government has certain rights in the invention.

BACKGROUND OF THE INVENTION

The adhesion of mammalian cells to the extracellular matrix is of fundamental importance in regulating growth, adhesion, motility and the development of proper cellular phenotype. This has implications for normal development, wound healing, chronic inflammatory diseases, and tumor metastasis. Evidence accumulated over the last several years suggests that the molecular basis for the adhesion of both normal and transformed cells is complex and probably involves several distinct cell surface molecules. Extracellular matrices consist of three types of macromolecules: collagenous glycoproteins, proteoglycans and noncollagenous glycoproteins.

One noncollagenous adhesive glycoprotein of interest is laminin. Laminin is a high molecular weight (~850,000) extracellular matrix glycoprotein found almost exclusively in basement membranes. (Timpl et al., *J. of Biol. Chem.*, 254: 9933-9937 (1979)). The basement membrane is an ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation, and differentiation, while migratory cells, both normal and neoplastic, must traverse the basement membrane in moving from one tissue to another.

Laminin consists of three different polypeptide chains: B1 with 215,000 MW, B2 with 205,000 MW and A with 400,000 MW (Timpl and Dziadek, *Intern. Rev. Exp. Path.*, 29: 1-112 (1986)). When examined at the electron microscopic level with the technique of rotary shadowing, it appears as an asymmetric cross, with three short arms 37 nm long, each having two globular domains, and one long arm 77 nm long, exhibiting a large terminal globular domain (Engel et al., *J. Mol. Biol.*, 150: 97-120 (1981)). The three chains are associated via disulfide and other bonds. Structural data shows that laminin is a very complex and multidomain protein with unique functions present in specific domains.

Laminin is a major component of basement membranes and is involved in many functions. Laminin has the ability to bind to other basement membrane macromolecules and therefore contributes to the structural characteristics of basement membranes. Laminin has been shown to bind to type IV collagen (Charonis et al., *J. Cell. Biol.*, 100: 1848-1853 (1985); Laurie et al., *J. Mol. Biol.*, 189: 205-216 (1986)) exhibiting at least two binding domains (Charonis et al., *J. Cell. Biol.*, 103: 1689-1697 (1986) Terranova et al., *Proc. Natl. Acad. Sci. USA*, 80: 444-448 (1983). Laminin also binds to entactin/nidogen (Timpl and Dziadek, supra and to basement membrane-derived heparin sulfate proteoglycan (Laurie et al., supra.). Laminin also has the ability to self-associate and form oligomers and polymers. Yurchenco et al., *J. Biol. Chem.*, 260: 7636-7644 (1985). Another important functional aspect of laminin is its ability to associate with cell surface molecular receptors and consequently modify cellular phenotype in various ways. A receptor for laminin with a molecular weight of about 68,000 has been observed in various cell types (Lesot et al., *EMBO. J.*, 2: 861-865 (1983); Malinoff and Wicha, *J. Cell. Biol.*, 96: 1475-1479 (1983). However, at least one other and maybe more cell surface receptors for laminin may exist. [See Timpl and Dziadek, supra; Horwitz et al., *J. Cell. Biol.*, 101: 2134-2166 (1985)]. These might include sulfatides, gangliosides [Roberts et al., *Proc. Natl. Acad. Sci. USA*, 82: 1306-1310 (1985)] or various proteins and proteoglycans. These cell surface molecules may be mediators for the various effects that laminin has on cells. It is known that laminin can directly promote cell adhesion and cell migration of various cell types ranging from normal and malignant mesenchymal cells such as fibroblast and endothelial cells, to various epithelial cells Timpl and Dziadek, supra. However, the exact domains of laminin involved in such processes are not well established yet. Although, it is known that a heparin binding site exists on the A-chain, in the globule of the long arm of laminin (Ott et al., *Eur. J. Biochem.*, 123: 63-72 (1982)), its exact amino acid sequence is not identified yet.

Recently, a laminin fragment having a binding domain for a cell receptor without having a binding domain for type IV collagen has been described. U.S. Pat. No. 4,565,789 to Liotta et al. The Liotta patent discloses laminin fragments obtained by digestion of laminin with pepsin or cathepsin G. More specifically, digestion of laminin with pepsin or cathepsin G produces P1 ($M_r$, 280,000) and C1 ($M_r$, 350,000) fragments, wherein the long arm of the molecule is removed and also the globular end regions of the short arms are altered. C1 and P1 fragments having similar molecular weights and binding capacities can also be obtained by digestion of laminin with plasmin and chymotrypsin. Laminin is also known to stimulate neurite outgrowth, a function that has been primarily assigned to the lower part of the long arm of laminin (Edgar et al., *EMBO J.*, 3: 1463-1468 (1986)).

The functions that have been described above make laminin an important component of many diverse and clinically important processes such as cell migration, wound healing, nerve regeneration, tumor cell metastasis through vascular walls [Liotta, *Am. J. Path.*, 117: 339-348 (1984); McCarthy et al., *Cancer Met. Rev.*, 4: 125-152 (1985)], diabetic microangiopathy, and vascular hypertrophy due to hypertension. Laminin could also be used in various devices and materials used in humans. In order to better understand the pathophysiology of these processes at the molecular level, it is important to try to assign each of the biological activities that laminin exhibits to a specific subdomain or oligopeptide of laminin. If this can be achieved, potentially important pharmaceuticals based on small peptides producing specific functions of the native, intact molecule, can be synthesized.

Therefore, a need exists to isolate and characterize peptides which are responsible for the wide range of biological activities associated with laminin. Such lower molecular weight oligopeptides would be expected to be more readily obtainable and to exhibit a narrower profile of biological activity than laminin itself, thus increasing their potential usefulness as therapeutic or diagnostic agents.

BRIEF DESCRIPTION OF THE INVENTION

The present invention provides a polypeptide (AC 15) which represents a fragments of the B1 chain of laminin. This polypeptide can be prepared by conventional solid phase peptide synthesis. The formula of the polypeptide is:

arg—ile—gln—asn—leu—leu—lys—ile—thr—asn—leu—arg—
ile—lys—phe—val—lys.            (AC15)

Polypeptide AC15 formally represents isolated laminin residues 202-218 from the B1 chain of laminin. The single letter amino acid code for this polypeptide is RIQNLLKITNLRIKFVK.

This synthetic polypeptide was assayed for biological activity and found to be an extremely potent promoter of heparin binding to synthetic substrates and of cell adhesion of melanoma and endothelial cells. Therefore, it is believed that polypeptide AC15 may be useful to (a) promote cellular attachment to culture substrata (b) inhibit the metastasis of malignant cells, and (c) promote wound healing and implant acceptance. Since other cell types are expected to show similar behavior, other uses of peptide AC15 might be envisioned, such as assistance in nerve regeneration. Furthermore, since it is expected that further digestion/hydrolysis of peptide AC15 in vitro or in vivo will yield fragments of substantially equivalent bioactivity, such lower molecular weight peptides are also considered to be within the scope of the present invention.

BRIEF DESCRIPTION OF THE DRAWINGS

FIG. 2 depicts the primary amino acid sequence of the B1 chain of laminin.

DETAILED DESCRIPTION OF THE INVENTION

Structure of Laminin and the B1 Chain

Figure 1:
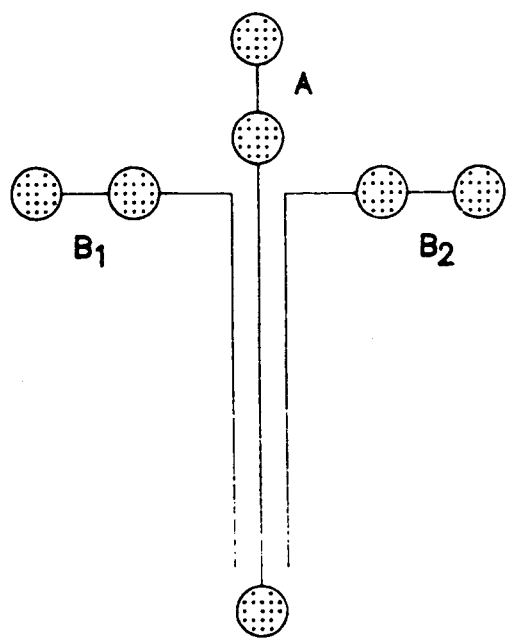
FIG. 1 is a diagrammatic depiction of laminin, indicating the relative location of the A, B1 and B2 chains including globular regions located on each chain.

Referring to FIG. 1, when examined by the electron microscope utilizing rotary shadowing techniques, the structure of laminin appears as an asymmetric cross. The three short arms each have two globular domains and are 37 nm in length. The long arm exhibits one large terminal globular domain and is 77 nm in length. Engel et al., supra. As seen in FIG. 1 the three chains are associated via disulfide bonds and other bonds. All three polypeptide chains of laminin have now been sequenced. Sasaki et al., supra; Sasaki and Yamada, J. Biol. Chem. 262, 17111 (1987); Sasaki et al., J. Biol. Chem. 263, 16536 (1988). Taken together, the three chains are composed of a total of 6,456 amino acid. The complete sequence of the B1 chain is shown in FIG. 2.

Binding sites for heparin are of special interest since heparin-like macromolecules such as heparan sulfate proteoglycans are present in basement membranes and cell surfaces and therefore their association with laminin may affect basement membrane structure and diverse cellular functions.

In the past, using as criteria (a) the hydropathy index of a sequence and (b) the number of argines and lysines present in a sequence, areas from the B1 chain were selected, synthetic peptides made and checked for their ability to bind to heparin and to affect cell adhesion (Charonis et al. J. Cell Biol 107: 1253, 1988). However this approach suffers from two drawbacks: First, because of the large number of amino acids present in laminin it is extremely time consuming and expensive to make and test synthetic peptides fulfilling these criteria; second, we have found out in the previously used approach that the first criterion, the hydropathy index of a sequence is not reliable.

Identification of heparin binding sequences by rotary shadow electron microscopy.

Figure 4:
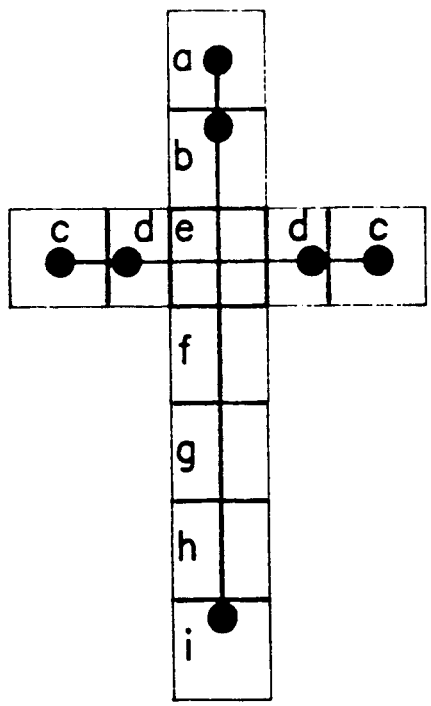
FIG. 4 is a graph showing the division of the laminin molecule to domains, in order to perform statistical analysis of heparin-binding.
Figure 3A:
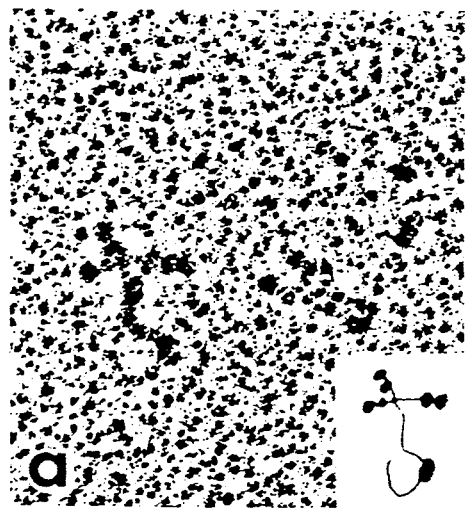
FIG. 3 is a composite showing various heparin molecules binding to laminin molecules.
Figure 3C:
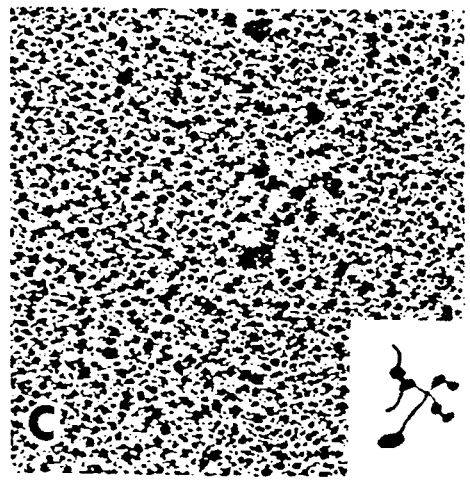
Figure 3E:
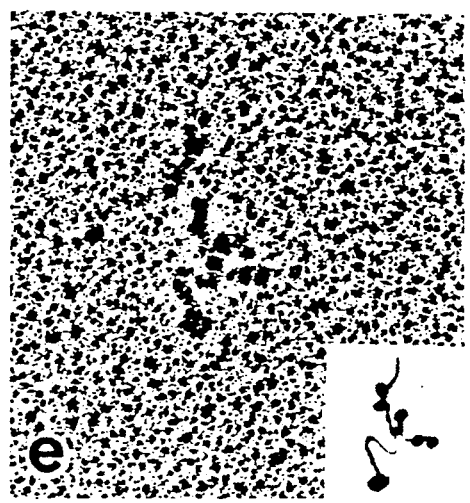
Figure 3B:
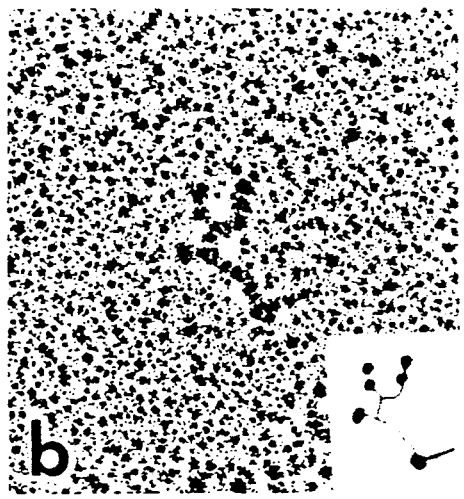
Figure 3D:
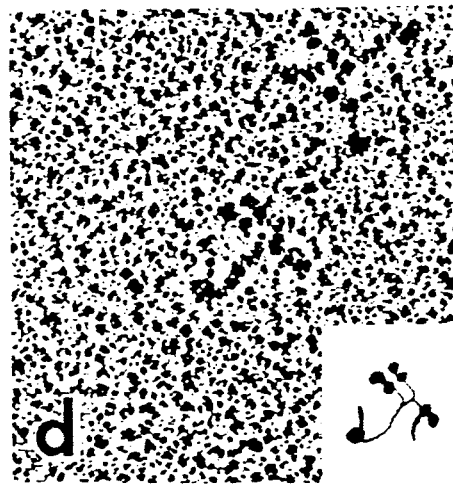
Figure 3F:
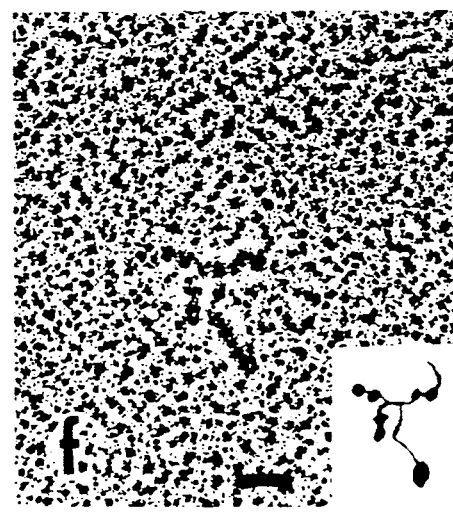
Figure 5:
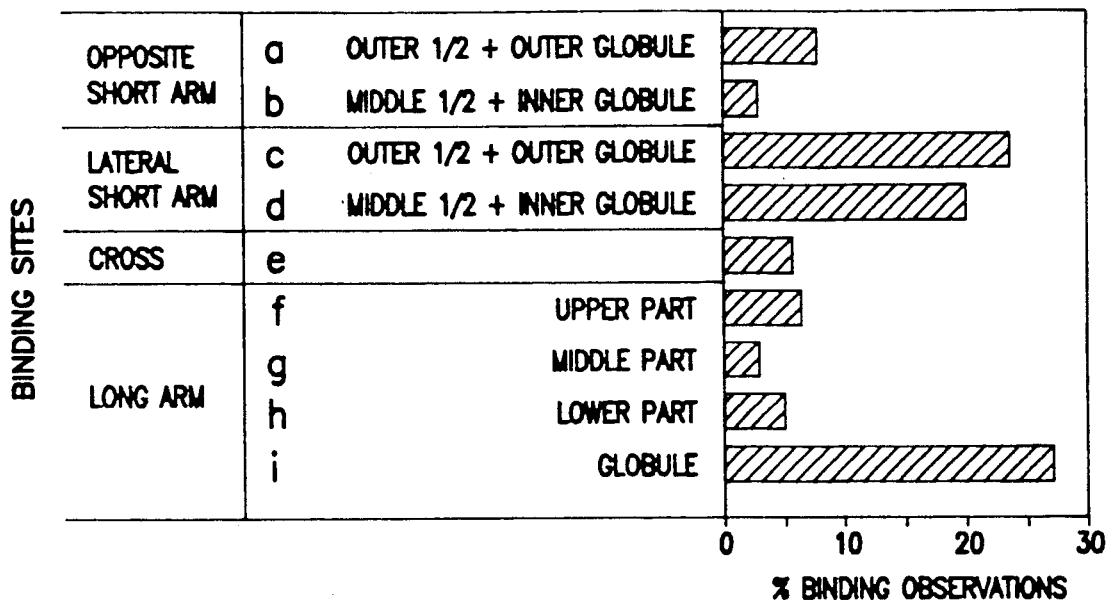
FIG. 5 is a graph showing the statistical analysis of the heparin binding to laminin.
Figure 6:
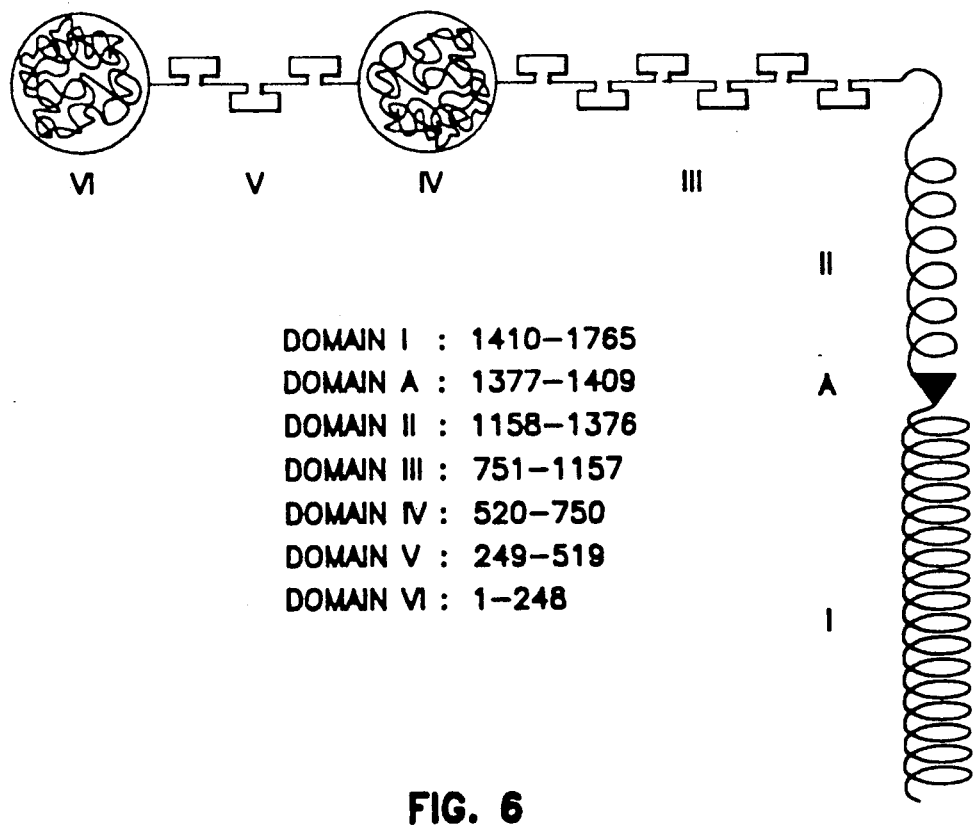
FIG. 6 shows the organization of domains on the laminin B1 chain.

In order to overcome these difficulties, we decided to use the technique of rotary shadow electron microscopy, in order to look for heparin-binding regions with an advised mind. This technique (Shotton et al, J. Mol. Biol. 131: 303, 1979) allows the direct observation of binding events and the mapping of these events on restricted domains. We incubated laminin and heparin at various molar ratios and examined their interactions at the electron microscopic level. FIG. 3 is a composite showing a variety of such interactions. Because some of these interactions may be non-specific, due to simple superimposition of these macromolecules, we decided to precisely map these binding events, in order to see in which areas on the laminin molecule the frequency of binding events was above background levels, therefore it could be considered specific. FIG. 4 is a graph showing the areas in which the laminin molecule was divided. After careful examination at the electron microscopic level, we recorded 187 binding events and constructed a histogram, shown in FIG. 5. This histogram revealed to us that a novel heparin binding site exists on the outer globule of one of the lateral short arms. (i.e. Domain VI; see FIG. 6) Various peptides were synthesized from these regions of the B1 and B2 chains of laminin, tested as previously described (Charonis et al, supra); one of them, peptide AC15, was positive in these assays. According to the present invention, we have synthesized peptide AC15, which corresponds to residues 202-218 of the B1 chain of laminin and found that this peptide exhibits very strong heparin-binding and cell attachment promoting activity.

Synthesis of the Polypeptide. The polypeptide of the invention was synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2d ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0 M acetic acid, followed by lyophilization of the extract. Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples.

EXAMPLE 1

Heparin Binding to Plastic Plates Coated with Peptide AC15

Figure 7:
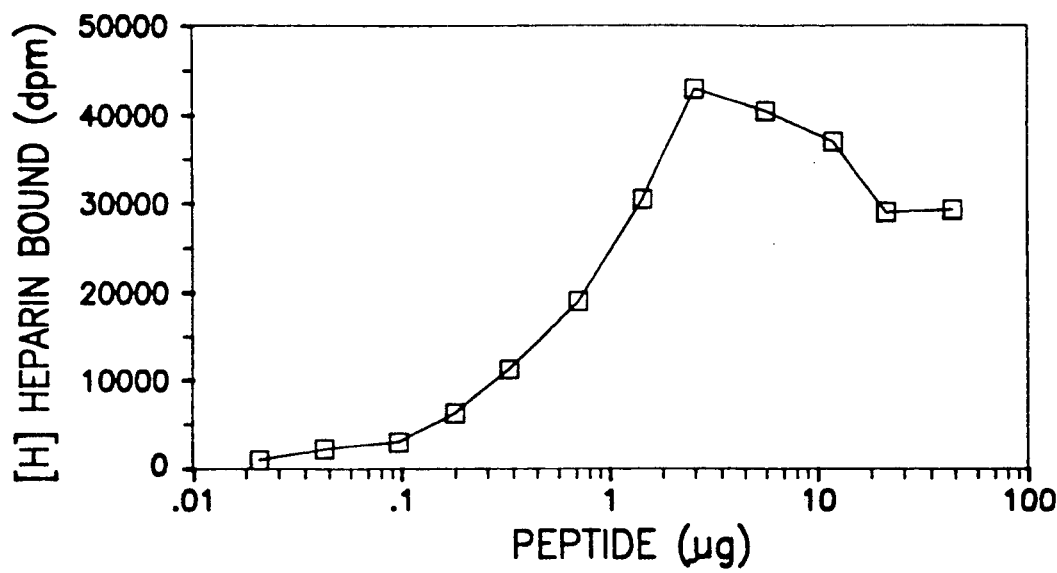
FIG. 7 is a graph showing the direct binding of heparin to peptide AC15 coated on plastic plate in various concentrations.

In order to test the ability of the synthesized peptide AC15 to bind to 96-well plastic plates (in which experiments with cultured cell lines can be performed), we did the following experiment. Stock solution of peptide AC15 at a maximum concentration of 50 µg/ml were prepared and serially diluted in PBS+$NaN_3$ producing final concentration from 50 µg/ml to 0.025 µg/ml. Fifty µl from each concentration was coated on the 96-well plates and left to dry overnight at 28° C. Then, wells were treated for two hours with 200 ml of 2 mg/ml BSA and 6 mM phosphate, 100 mM NaCl, 68 µM $CaCl_2$, pH 6.8 (wash buffer) in order to minimize non-specific binding. Next 50 µl of $^3$H-heparin (10 µg/ml) was added (50,000 cpm/well) for two hours at 37° C. The wells were then washed three times with wash buffer containing 0.05% Triton X-100 and finally they were incubated for thirty minutes at 60° C. with 200 µl of 0.5 N NaOH and 1% SDS. The amount of $^3$H-heparin bound at each peptide concentration was quantitated with a Beckman LS-3801 liquid scintillation counter. The results shown in FIG. 7 indicate that peptide AC15 is a very potent binder of heparin. Comparison with data obtained in the past using exactly the same methodology indicate that peptide AC15 is at least 10 times stronger than peptide F-9 [Charonis et al., *J. Cell Biol.* 107: 1253 (1988)] and 100 times stronger than laminin, when used in the same coating concentrations.

EXAMPLE 2

Inhibition of Heparin Binding to Laminin by Peptide AC15

Figure 8:
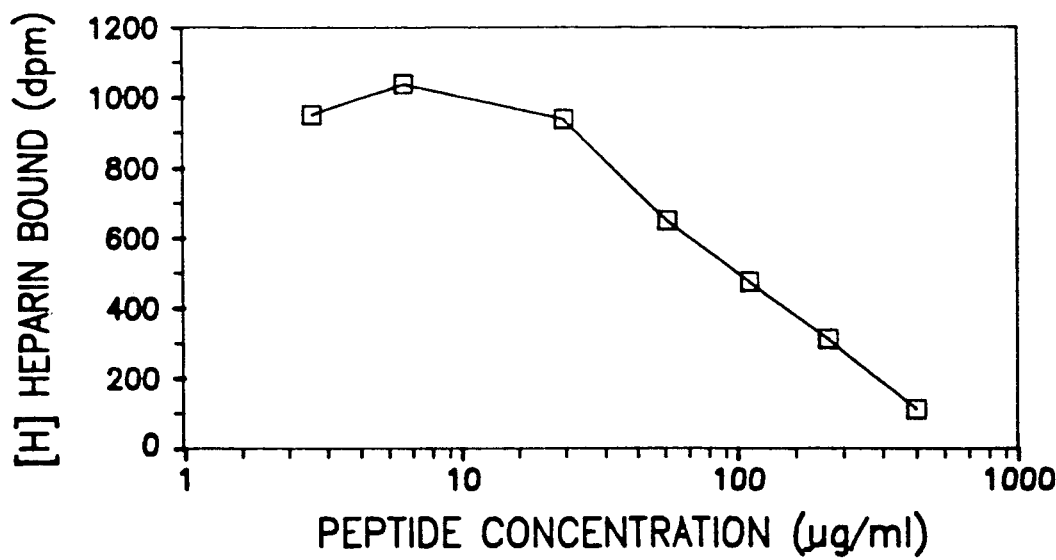
FIG. 8 is a graph showing the inhibition of binding of heparin to native laminin coated on plastic by various concentrations of peptide AC15 present in solution.

Peptide AC15 in solution (and not absorbed to plastic), was screened for the ability to inhibit the binding of heparin to intact, native laminin coated on plastic. This experimental approach avoid problems due to differential coating of peptides in heparin binding assays. Laminin at 60 µg/ml in PBS was coated on 96-well plates, using 50 µl per well and dried overnight at 28° C. The wells were then treated for two hours with 2 mg/ml BSA in wash buffer (described above in Example 1). Peptide AC15 at various dilutions ranging from 0.5 mg/ml to 5 µg/ml in PBS and CHAPS (cholamido-propyl-dimethyl-ammonio-propane-sulfonate) (a detergent used to avoid non-specific sticking) was co-incubated with a standard amount of $^3$H-heparin (10,000 cpm per well 5 µg/ml final concentration) for two hours at 37° C. and the mixture was then transferred to the laminin coated plate (50 µl) and allowed to incubate for another two hours at 37° C. The wells were then washed and radioactivity was counted as described above. The results shown in FIG. 8 indicate that peptide AC15 is a strong inhibitor of heparin binding to laminin. These results also suggest that peptide AC15 can bind to heparin not only when coated on plastic, but also when present in solution. Other peptides of similar length and hydropathy index when tested with this assay were unable to compete for the binding of heparin to laminin-coated plastic.

EXAMPLE 3

Heparin/Peptide Interaction Specificity

Figure 9:
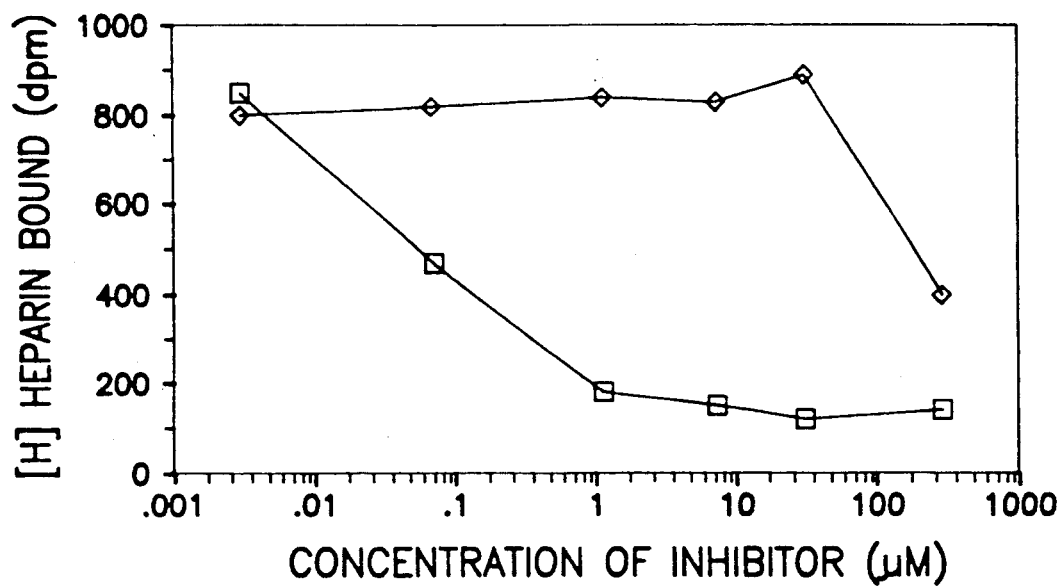
FIG. 9 is a graph depicting the competition of binding of heparin to peptide AC15 coated on plastic, by glycosaminoglycans in various concentrations.

To check whether charge was the main factor in the interaction between heparin and peptide AC15 or whether the heparin structure was also critical to this interaction, heparin along with one other sulfated glucosaminoglycan, chondroitin sulfate were used in competition experiments. A standard amount of 3 µg per well of peptide AC15 was coated on 96-well plates as described above. Wells were treated for two hours with 2 mg/ml BSA in wash buffer. Then, a final volume of 50 µl was added to each well, containing a standard amount of $^3$H-heparin (5,000 cpm per well) and various amounts of non-radioactive heparin, and chondroitin sulfate. After incubating for two hours at 37° C., the wells were washed and radioactivity was counted as described above in Example 1. FIG. 9 shows that unlabeled heparin is able to compete for the binding of tritiated heparin to peptide AC15 at very low concentrations, whereas chondroitin sulfate cannot mimic this effect even at very high concentrations. These results suggest that not only the charge, but also the conformation of the glucosaminoglycan is crucial for this interaction.

EXAMPLE 4

Adhesion of Cancer Cells

Highly metastatic murmine melanoma cells, K-1735-M4 were originally provided by Dr. I. J. Fidler of Anderson Hospital, University of Texas Health Sciences Center, Houston, Tex. When the cells were received, a large number of early passage cells were propagated and frozen in liquid nitrogen. The tumor cells are usually cultured in vitro for no longer than six weeks. Following this period, the cells are discarded and new cells withdrawn from storage for use in further in vitro or in vivo experiments This precaution is taken to minimize phenotypic drift that can occur as a result of continuous in vitro passage. The cells were cultured in Dulbecco,s Modified Eagle's Medium containing 5% heat inactivated fetal calf serum. The cultures were grown in 37° C. incubators with a humidified atmosphere containing 5% $CO_2$. Cells were subcultured twice weekly by releasing cells gently from the flask, using 0.05% trypsin and 1 mM EDTA.

Figure 10:
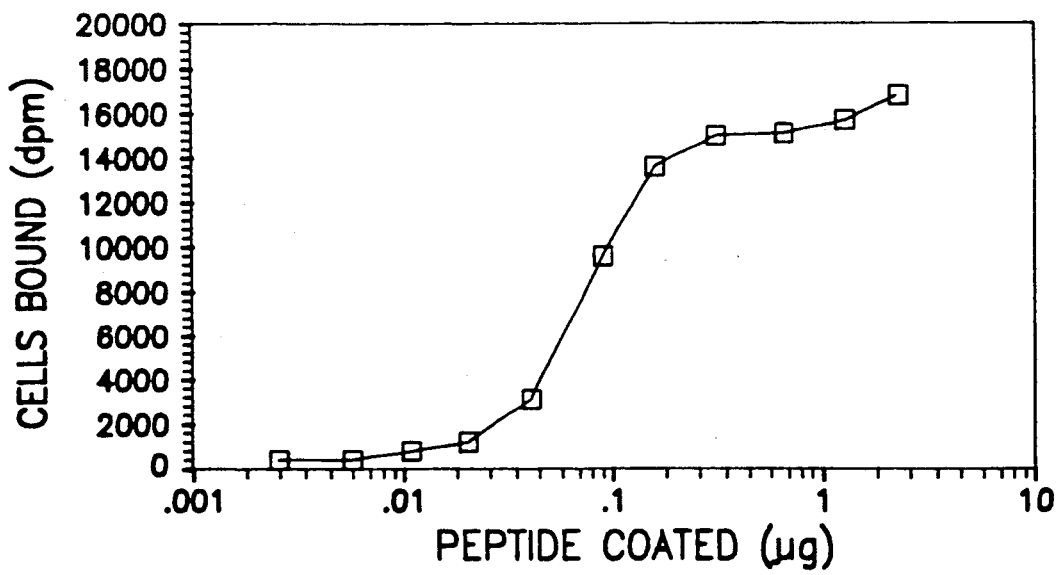
FIG. 10 is a graph depicting the direct binding of melanoma cells to plastic coated with polypeptide AC15.

Cultures of cells which were 60–80% confluent were metabolically labeled for 24 hours with the addition of 3 mCi/ml of $^3$H-td (tritiated thymidine). On the day of the assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells adjusted to a concentration of $3-4 \times 10^4$/ml, and 100 µl of this cell suspension was added to the wells coated with peptide AC15 at various concentrations. The assay mixture was then incubated at 37° C. for 120 minutes. At the end of the incubation, the wells were washed with warm PBS containing 10 mM $Ca^{++}$, and the adherent population was solubilized with 0.5 N NaOH contained 1% sodium dodecyl sulfate. The solubilized cells were then quantitated using a liquid scintillation counter. As shown in FIG. 10, increasing peptide concentrations produced a higher percentage of cell adhesion with a tendency to plateau at coating concentrations above 0.5 µg/ml.

EXAMPLE 5

Figure 11:
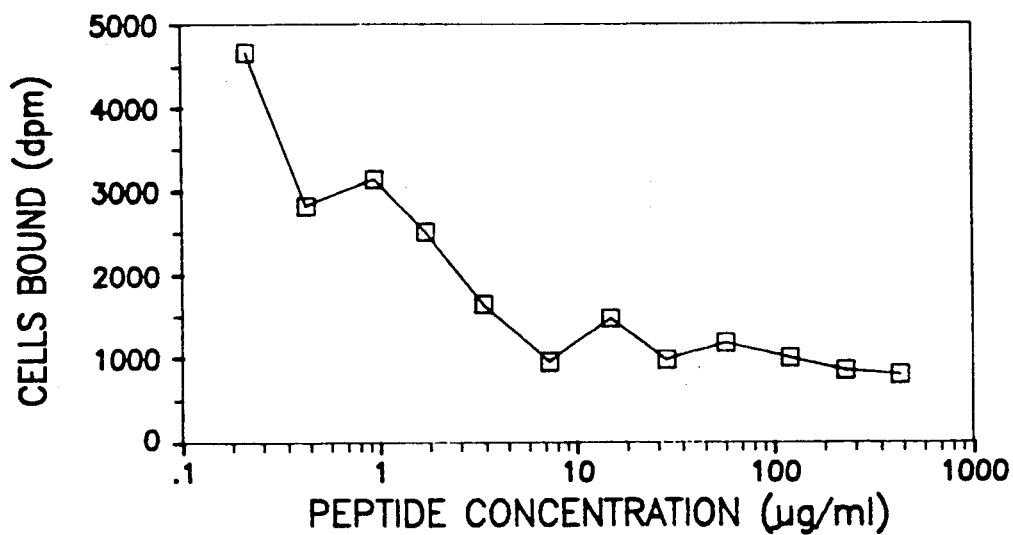
FIG. 11 is a graph depicting the competition of binding of melanoma cells to laminin-coated plastic in the presence of various concentrations of peptide AC15 in solution.

Inhibition of Adhesion of Cancer Cells in the Presence of Peptide AC15 in solution In order to test the ability of peptide AC15 to demonstrate its function when present in solution, we used the melanoma cell line described above (M4). Cells were grown, labeled and harvested as described in Example 4, but after detachment and washing they were coincubated for 20 min in the presence of various concentrations of peptide AC15 in solution. They were then applied for another 20 min on laminin-coated plastic wells. At the end of the incubation the same treatment described in EXAMPLE 4 were used. As shown in FIG. 11, increasing concentrations of peptide AC15 were able to dramatically decrease the binding of melanoma cells to laminin-coated substrata.

EXAMPLE 6

Effect of Peptide AC15 in the Adhesion of Endothelial Cells

A. Isolation of Bovine Aortic Endothelial Cells.

Bovine aortic endothelial cells were isolated according to the following protocol. Aortas were obtained from a local slaughterhouse, washed in cold phosphate buffered saline (PBS) (136 mM NaCl, 2.6 mM KCl, 15.2 mM $Na_2HPO_4$, pH 7.2 and processed within 2 hours. Crude collagenase (CLS III, 125–145 units per mg dry weight, Cooper Biomedical) was used at 2 mg/ml in Dulbecco's modified Eagle's medium (DMEM) (GIBCO). The vessel was clamped at the distal end, filled with the collagenase-PBS solution and digestion was carried out for 10 minutes. The lumenal contents were harvested, followed by the addition of fresh collagenase for two additional 10-minute periods. The enzyme-cell suspensions were added to an equal volume of DMEM containing 10% fetal bovine serum (FBS) to inhibit the enzyme and spun in a centrifuge at $400 \times g$ for 10 minutes. The resulting cell pellet was resuspended in DMEM containing 10% FBS, 100 units/ml of penicillin G, 100 µg/ml of streptomycin and 100 µg/ml of crude fibroblast growth factor. Cells are cultured in 75 cm$^2$ flasks in a humidified 5% $CO_2$ atmosphere at 37° C. Cultures were fed twice a week with the same medium and cells were used in assays when approximately 75% confluent. Cells were identified as endothelial in nature by characteristic cobblestone morphology, contact inhibition of growth upon reaching confluency, and positive immunofluorescent staining for factor VIII:RAg (Miles Laboratories) ([Schwartz, In Vitro 14:966, 1978). Only endothelial cells, megakaryocytes and platelets are known to contain the factor VIII:RAg. This method routinely gives a high yield of endothelial cells with little contamination (less than 5%) by smooth muscle cells, pericytes or fibroblasts as judged by phase contrast microscopy as well as by immunostaining.

B. Inhibition of Adhesion of Bovine Aortic Endothelial Cells to Laminin by Peptide AC15.

Inhibition of adhesion was measured using 96 well microtiter plates. In each well 50 µl of a laminin solution of 60 µg/ml were absorbed by incubating overnight at 29° C.

Figure 12:
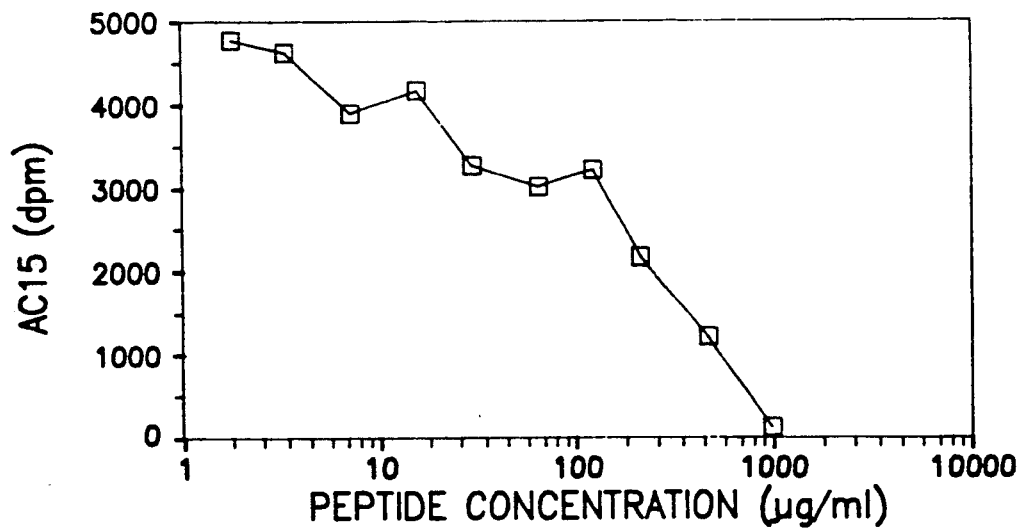
FIG. 12 is a graph depicting the competition of binding of endothelial cells to laminin-coated plastic in the presence of various concentrations of peptide AC15 in solution.

Cultures of cells which were 60–80% confluent were metabolically labeled for 24 hours with the addition of 3mCi/ml of $^3$H-amino acid mixture. On the day of assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells were adjusted to a concentration of $3-4 \times 10^4$/ml, and 50 μl of this cell suspension was added to 50 μl of various concentrations of peptide AC15 in the same buffer at 37° C. After 15 min of co-incubation, 50 μl of the mixture was applied to the laminin coated wells for 20 min at 37° C. At the end of the incubation, the wells were washed with warm PBS containing 10 mM $Ca^{++}$, and the adherent population was solubilized with 0.5 N NaOH containing 1% sodium dodecyl sulfate. The solubilized cells were then quantitated using a liquid scintillation counter. Each determination was done in triplicate. The results of this study are summarized in FIG. 12 below.

These results indicate that peptide AC15 is involved in the phenomenon of endothelial cell adhesion.

A number of practical applications for the polypeptides of the present invention can be envisioned. Such applications include the promotion of the healing of wounds caused by the placement of synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft, which is generally woven or knitted from nitrocellulose or polyester fiber, particularly Dacron TM (polyethylene terephthalate) fiber. Most types of cells are attracted to laminin and to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumae, e.g., spinal cord injuries.

In such cases, it may be advantageous to couple the peptide to a biological molecule, such as collagen, a glycosaminoglycan or a proteoglycan. It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, the polypeptides of the present invention can be used to promote cell adhesion of various cell types to naturally occurring or artificial substrata intended for use in vitro. For example, a culture substrate such as the wells of a microtiter plate or the medium contacting surface of microporous fibers or beads, can be coated with the cell-attachment polypeptides. This can obviate the use of laminin in the medium, thus providing better defined conditions for the culture as well as better reproducibility.

As one example of commercial use of cell-attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of coating protein in the growth medium and the present polypeptides are expected to provide an improved, chemically-defined coating for such purposes. Other surfaces or materials may be coated to enhance attachment, such as glass, agarose, synthetic resins or long-chain polysaccharides.

In the past, selected laminin domains have been studied for ability to decrease the metastatic potential of invasive cell lines (McCarthy et al, supra). This effect is mediated via the saturation and therefore neutralization of cell surface receptors for laminin. In accordance with the present invention, the data presented herein suggest that receptors for the polypeptide AC 15 should exist on cell surfaces of malignant cells. Consequently, this polypeptide could be used to block laminin receptors of metastatic cells and therefore reduce their metastatic potential.

The invention has been described with reference to various specific and preferred embodiments and techniques. However, it should be understood that many variations and modifications may be made while remaining within the spirit and scope of the invention.

What is claimed is:

1. A polypeptide of the formula:

arg—ile—gln—asn—leu—leu—lys—ile—thr—asn—leu—arg—ile—lys—phe—val—lys.

* * * * *